(12) United States Patent
Horn et al.

(10) Patent No.: US 7,341,830 B2
(45) Date of Patent: Mar. 11, 2008

(54) METHOD AND REAGENT SYSTEM HAVING A NON-REGENERATIVE ENZYME-COENZYME COMPLEX

(75) Inventors: Carina Horn, Biblis (DE); Joachim Hoenes, Zwingenberg (DE); Wolfgang-Reinhold Knappe, Ludwigshafen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 10/514,451

(22) PCT Filed: May 16, 2003

(86) PCT No.: PCT/EP03/05178

§ 371 (c)(1),
(2), (4) Date: May 26, 2005

(87) PCT Pub. No.: WO03/097864

PCT Pub. Date: Nov. 27, 2003

(65) Prior Publication Data

US 2005/0214891 A1    Sep. 29, 2005

(30) Foreign Application Priority Data

May 16, 2002   (DE)   ................ 102 21 840
May 16, 2002   (DE)   ................ 102 21 845
May 16, 2002   (DE)   ................ 102 21 846

(51) Int. Cl.
C12Q 1/00   (2006.01)
C12Q 1/32   (2006.01)

(52) U.S. Cl. ............................ 435/4; 435/26
(58) Field of Classification Search .................... None
See application file for complete search history.

(56) References Cited

U.S. PATENT DOCUMENTS 3,964,974 A * 6/1976 Banauch et al. .............. 435/4
4,451,568 A * 5/1984 Schneider et al. .......... 435/181
4,820,399 A * 4/1989 Senda et al. ............ 204/403.09
4,919,767 A * 4/1990 Vadgama et al. ........... 205/778
5,340,722 A   8/1994 Wolfbeis et al.
5,447,847 A   9/1995 Yamada et al.

FOREIGN PATENT DOCUMENTS

| DE | 41 18 880 A    | 12/1992 |
| EP |    327952 A1 * | 8/1989  |
| EP | 0 691 408 A1   | 1/1996  |
| EP | 0 691 408 B1   | 1/1996  |
| JP |    7115997     | 5/1995  |
| JP |    7115998     | 5/1995  |
| JP |    9248200     | 9/1997  |
| JP | 2000035413     | 2/2000  |
| JP | 2001149092     | 6/2001  |

OTHER PUBLICATIONS

Sigma-Aldrich Company Website, Nicotinamide adenine dinucleotide Product information, 2006□□http://www.sigmaaldrich.com/catalog/search/ProductDetail/SIGMA/N6754.*

D'Auria Sabato et al: "The fluorescence emission of the apo-glucose oxidase from *Aspergillus niger* as probe to estimate glucose concentrations". Biochemical and Biophysical Research Communications, Academic Press Inc. Orlando, FL, US, vol. 263, No. 2, 1999, pp. 550-553, XP002158779; ISSN: 0006-291X.

Sierra et al: "Determination of Glucose in Blood on the Instrinsic Fluorescence of Glucose Oxidase". Analytical Chemistry, vol. 69, No. 8, Apr. 15, 1997, pp. 1471-1476.

Narayanaswamy et al: "An Optical Fibre Probe for the Determination of Glucose Based on Immobilized Glucose Dehydrogenase". Analytical Letters, 21(7), 1998, pp. 1165-1175.

* cited by examiner

*Primary Examiner*—Jon Weber
*Assistant Examiner*—Paul Martin
(74) *Attorney, Agent, or Firm*—Jill L. Woodburn; Richard T. Knauer; Sujatha Subramaniam

(57) ABSTRACT

The invention relates to a method and reagent system for detecting an analyte in a sample by means of an enzymatic reaction, involving the use of an enzyme-coenzyme complex as a stoichiometric reaction partner for the analyte present in the sample.

17 Claims, 5 Drawing Sheets

METHOD AND REAGENT SYSTEM HAVING A NON-REGENERATIVE ENZYME-COENZYME COMPLEX

CROSS REFERENCE TO RELATED APPLICATIONS

Figure 1:
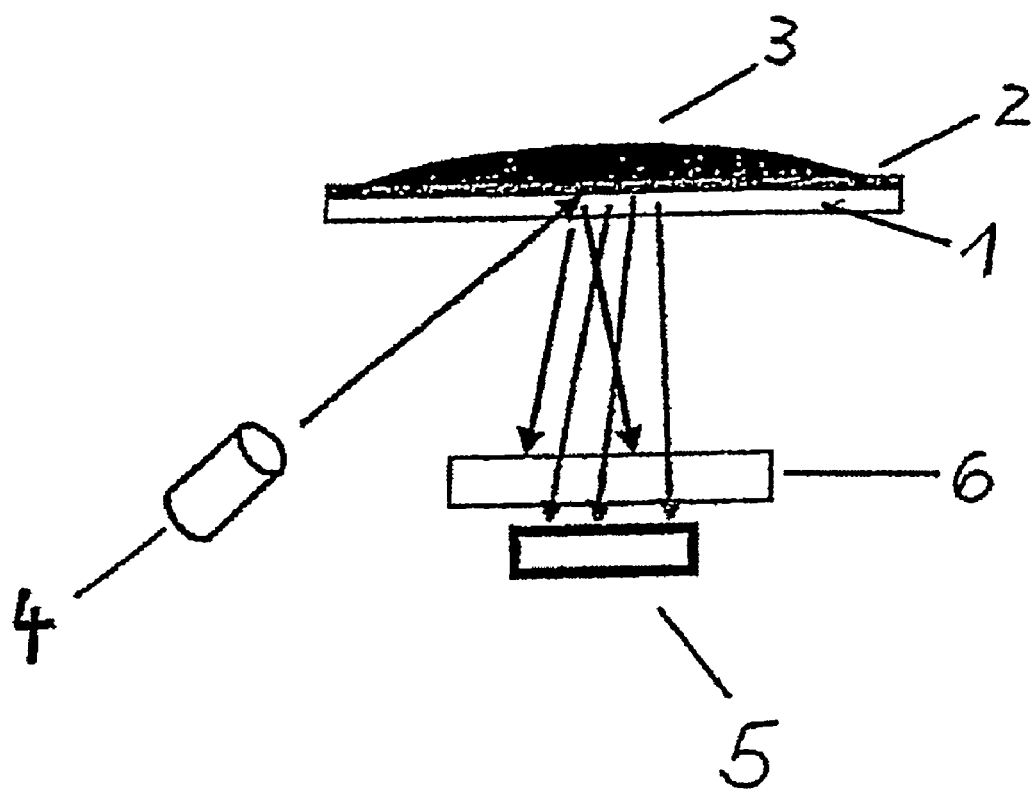

This application is a 371 of PCT/EP03/05178 filed May 16, 2003 and claims priority to foreign applications GERMANY 102-21-845.5 filed May 16, 2002, GERMANY 102-21-804.4 filed May 16, 2002 and GERMANY102-21-846.3 filed Mar. 10, 2002.

The invention relates to a method and a reagent system for detecting an analyte in a sample through an enzymatic reaction, comprising the use of an enzyme-coenzyme complex as non-regenerable, in particular stoichiometric reactant for the analyte present in the sample.

The detection of analytes, for example glucose in blood, by enzymatic methods is known. These entail the analyte to be determined being brought into contact with a suitable enzyme and a coenzyme, the enzyme being employed in catalytic amounts. The redox equivalents produced on reduction or oxidation of the coenzyme are transferred to mediators which are then detected electrochemically or photometrically in a further step. A calibration provides a direct connection between the measurement and the concentration of the analyte to be determined.

Sierra et al. (Anal. Chem. 69 (1997), 1471-1476) describe a determination of blood glucose based on the intrinsic fluorescence of glucose oxidase. In this method too, the enzyme is employed together with its coenzyme FAD in catalytic amounts, with redox equivalents being transferred to oxygen as mediator.

Narayanaswamy et al. (Analytical Letters 21 (7) (1988), 1165-1175) describe a fluorescence measurement with glucose dehydrogenase and NAD for glucose determination. The enzyme is in this case employed in catalytic, i.e. non-stoichiometric, amounts. The fluorescence measurement detects the free NADH in the solution.

It is possible through the electrochemically active substances (mediators) required for the prior art detection systems to detect the analytes to be determined only indirectly, i.e. via a plurality of chemical reactions. For this purpose, a complicated adjustment of the concentrations of the substances involved to optimize the reaction rate is often necessary. There is moreover the risk that the required electrochemically active substances are unstable on prolonged storage.

The mediators often also have to be employed in large excess relative to the enzyme-coenzyme system. The coenzyme has a high reactivity, so that the enzymic activity declines markedly on decomposition of the mediator, even in small amounts, e.g. <1% or on exposure to foreign substances, e.g. volatilization of the substances from packaging materials. This may lead to false signals in the determination of the analyte. Yet a further disadvantage is that the determination times for the analytes are normally in the region of at least a few seconds, for example for glucose in the region of >4 s, and the required sample volumes are large, e.g. >0.5 µl.

The object on which the present invention was based is at least partly to avoid the described disadvantages of the prior art. It was particularly intended to provide a non-sensitive and rapid method for the enzymatic detection of analytes, which leads to reliable measurement results even in the absence of mediators or/and indicators.

This object is achieved by using an enzyme-coenzyme complex as stoichiometric reactant instead of, as usual, as catalyst. Detection of the analyte requires only a single reaction step and is therefore extremely fast. The use of mediators and indicators, associated with the employment of complex reaction mixtures, with low stability and high susceptibility to interference, is no longer necessary.

One aspect of the invention is thus a method for detecting an analyte in a sample by an enzymatic reaction, comprising the steps:
  (a) contacting the sample with a detection reagent comprising an enzyme-coenzyme complex, where no regeneration of the coenzyme takes place, and
  (b) detecting a reaction of the analyte through a change in the enzyme-coenzyme complex.

A further aspect of the invention is a reagent system for detecting an analyte in a sample, comprising:
  (a) a detection reagent comprising an enzyme-coenzyme complex, where no regeneration of the coenzyme takes place, and
  (b) a support to receive the detection reagent.

The present invention makes a simple qualitative or quantitative determination of analytes possible within a very short reaction time of, preferably, $\leq 5$ s, particularly preferably $\leq 1$ s, most preferably $\leq 0.1$ s. The reaction is carried out under conditions with which no regeneration of the coenzyme takes place during the determination. It is moreover possible for a molecule enzyme-coenzyme complex to react only with a single molecule of the analyte. The reaction is therefore expediently carried out in the absence of mediators or other substances able to bring about regeneration of the coenzyme.

The detection reagent comprises the enzyme-coenzyme complex in an amount sufficient to make qualitative or/and quantitative determination of the analyte possible according to the desired test format. In particular, for quantitative determination of the analyte, the enzyme-coenzyme complex is employed in an amount such that the number of reacting molecules of the enzyme-coenzyme complex correlates with the analyte concentration present in the sample. The enzyme-coenzyme complex is particularly preferably employed in an at least stoichiometric amount relative to the analyte present in the sample, preferably in a stoichiometric excess relative to the analyte. In this connection, the statement "in at least a stoichiometric amount" means that the size of the sample is adjusted relative to the number of molecules of the enzyme-coenzyme complex in such a way that, with the analyte concentrations to be expected in the sample, the number of molecules of the enzyme-coenzyme complex which react with the analyte correlates with the analyte concentration present in the sample. "Stoichiometric amount" preferably means that the number of molecules of the enzyme-coenzyme complex corresponds to the maximum number of analyte molecules to be expected in the investigative sample.

The method and the detection system permit the use of very small amounts of sample, for example sample volumes of $\leq 1$ µl, in particular $\leq 0.1$ µl. The sample can where appropriate also be diluted before contacting with the detection reagent.

The method and detection system of the invention is suitable for determining any analytes, for example parameters in body fluids such as, for example, blood, serum, plasma or urine, but also in effluent samples or foodstuffs. The method can also be carried out as wet test, e.g. in a cuvette, or as dry test on an appropriate reagent support.

The analytes which can be determined are any biological or chemical substances which are able to undergo a reaction, in particular a redox reaction, with an enzyme-coenzyme complex, such as, for example, glucose, lactic acid, malic acid, glycerol, alcohol, cholesterol, triglycerides, ascorbic acid, cysteine, glutathione, peptides etc.

The enzymatic reaction is preferably a redox reaction in which the coenzyme in the enzyme-coenzyme complex is reduced or oxidized. The enzyme preferably used for a reaction of this type is an oxidoreductase. The enzyme particularly preferably used is a dehydrogenase, for example selected from a glucose dehydrogenase (E.C.1.1.1.47), lactate dehydrogenase (E.C.1.1.1.27, 1.1.1.28), malate dehydrogenase (E.C.1.1.1.37), glycerol dehydrogenase (E.C.1.1.1.6), alcohol dehydrogenase (E.C.1.1.1.1) or amino-acid dehydrogenase, e.g. L-amino-acid dehydrogenase (E.C.1.4.1.5). Further suitable enzymes are oxidases such as, for example, glucose oxidase (E.C.1.1.3.4) or cholesterol oxidase (E.C.1.1.3.6).

Coenzymes for the purposes of the present invention are preferably organic molecules which are linked covalently or noncovalently to an enzyme and are changed, for example oxidized or reduced, by the conversion of the analyte. Preferred examples of coenzymes are flavin, nicotine and quinone derivatives, for example flavin nucleoside derivatives such as, for example, FAD, $FADH_2$, FMN, $FMNH_2$, etc., nicotine nucleoside derivatives such as, for example, $NAD^+$, $NADH/H^+$, $NADP^+$, $NADPH/H^+$ etc. or ubiquinones such as, for example, coenzyme Q, PQQ etc.

The change in the coenzyme through reaction with the analyte can in principle be detected in any manner. It is possible in principle to employ for this all methods known in the art for detecting enzymatic reactions. However, the change in the coenzyme is preferably detected by optical methods. Optical detection methods include for example measuring absorption, fluorescence, circular dichroism (CD), optical rotary dispersion (ORD), refractometry etc. The change in the coenzyme is particularly preferably detected by measuring the fluorescence. The fluorescence measurement is highly sensitive and makes it possible to detect even low concentrations of the analyte in miniaturized systems.

The method or detection system of the invention may comprise a liquid test, in which case the reagent is present for example in the form of a solution or suspension in an aqueous or nonaqueous liquid or as powder or lyophilizate. However, the method and detection system of the invention preferably comprises a dry test, in which case the reagent is applied to a support. The support may comprise for example a test strip comprising an absorbent or/and swellable material which is wetted by the sample liquid to be investigated.

In a particularly preferred embodiment, the detection reagent used is a gel matrix with an enzyme-coenzyme complex embedded therein. The gel matrix preferably has a layer thickness of $\leq 50$ µm, in particular $\leq 5$ µm, and is applied to a support, for example an at least partly optically transparent support. The gel matrix may be a matrix comprising one or more soluble polymers, as in known dry test systems (e.g. AccuChek Active), and can be produced by knife application and drying. The matrix is preferably a polymer with a structure based on photopolymerizable substances such as, for example, acrylic monomers, e.g. acrylamide or/and acrylic esters such as polyethylene glycol diacrylate, or vinylaromatic monomers, e.g. 4-vinylbenzenesulfonic acid, or combinations thereof. A gel matrix of this type can be produced by applying a liquid which contains the reagent, comprising enzyme, photopolymerizable monomer and, where appropriate, coenzyme, photoinitiator or/and unreactive constituents, to an at least partly optically transparent support, for example to a plastics sheet, and irradiating, for example with UV light from the reverse side, so that polymerization of the monomer or of the monomers takes place on the support up to a predefined layer thickness. The layer thickness can be controlled by adding absorbing substances to the reagent or/and through the duration or intensity of irradiation. Excess liquid reagent can be removed and reused after the polymerization (see, for example, FIG. 2).

On the other hand, the gel matrix can also be produced by conventional coating procedures, in which case the liquid reagent is applied to a support, brought to the desired thickness using suitable methods, e.g. using a knife, and then completely polymerized.

After inclusion by polymerization or embedding in the gel matrix, the enzyme is in a protected micro-environment. If the polymeric gel matrix is sufficiently crosslinked, the enzyme molecules are present in an immobilized form. Low molecular weight substances or glucose or other analytes or else coenzymes can, however, diffuse freely through the polymer network.

The enzyme can either be included together with its coenzyme by polymerization in the matrix or, after the polymerization, the matrix can be brought into contact with a solution of the coenzyme, so that the appropriate enzyme-coenzyme complex is formed. The concentration of the enzyme in the gel matrix is preferably chosen to be high enough for a stoichiometric reaction with the analyte to be determined, and a direct determination of the coenzyme which is changed by the reaction, to be possible. The reaction consists only of a single catalytic reaction, for example, a redox reaction, which can take place in the region of milliseconds or microseconds. The coenzyme which is changed by the reaction is optimally protected from interfering influences through binding to the active center of the enzyme and, where appropriate, additionally by embedding in the gel matrix.

The invention is additionally to be explained by the following figures and examples.

FIGURES

FIG. 1 shows a first embodiment of the detection system of the invention. A reagent layer (2), e.g. a gel matrix with an enzyme-coenzyme complex, is applied to an optically transparent support (1). The enzyme-coenzyme complex is in a form such that no regeneration of the coenzyme can take place during the analyte determination. A sample (3), e.g. blood, is put on the reagent layer. Determination of the enzymatic reaction between the analyte contained in the sample (3), and the enzyme-coenzyme complex contained in the reagent layer (2) takes place by optical methods. Light from a light source (4), e.g. a laser or an LED, is beamed from behind (through the support) onto the reagent layer (2). Absorption light or fluorescent light beamed back from the sample is detected in a detector (5). Where appropriate—in particular for detecting fluorescent light—an optical filter element (6) is put in front of the detector in order to block leakage of the fluorescence-exciting light.

Figure 2:
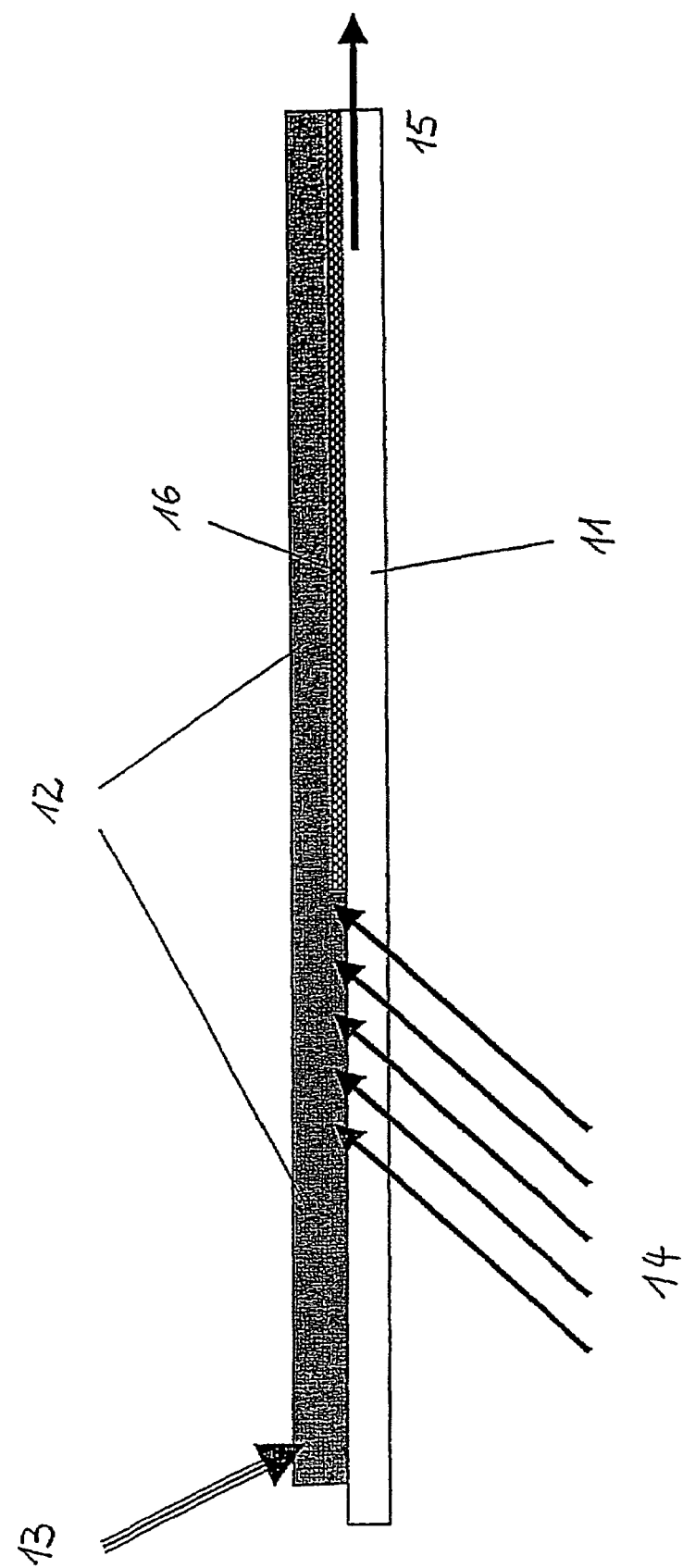

FIG. 2 shows the production of a detection system of the invention. A liquid reagent (12) is applied, for example in a first position (13), to an optically transparent support (11), e.g. a plastics sheet. The liquid reagent (12) is irradiated at a second position from below through the support (11) with light from a light source (14). At the same time, the support is moved in the direction (15) identified by the arrow. A polymerized reagent layer (16) is formed directly on the support (11). Excess liquid reagent is present above the polymer layer (16). The thickness of the polymerized reagent layer (16) can be controlled through the reagent composition, the duration and intensity of the beaming in of light, and through the properties of the support (11).

Figure 3:
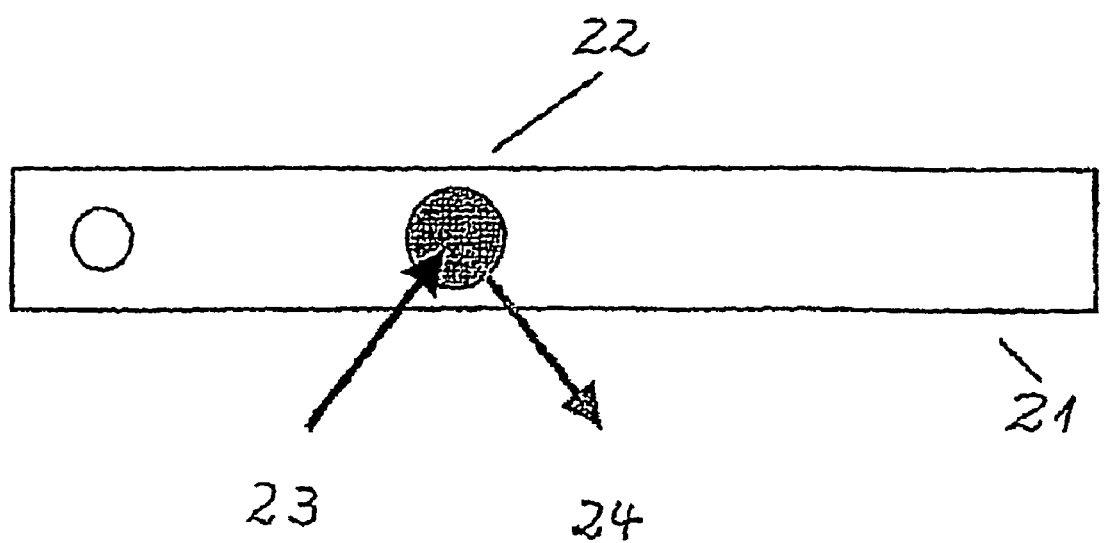

FIG. 3 shows an embodiment of a fluorescence-based sensor from below. A polymerized reagent layer, for example one produced by the continuous process in FIG. 2, can be cut and applied to a support (21) by use of known techniques. After application of the sample to the upper side, exciting light (23), e.g. UV light, is beamed in from a light source from below. The fluorescence (24), e.g. blue light, generated through the reaction of the analyte with the enzyme-coenzyme complex in the reagent layer (22) is detected with a detector.

Figure 4:
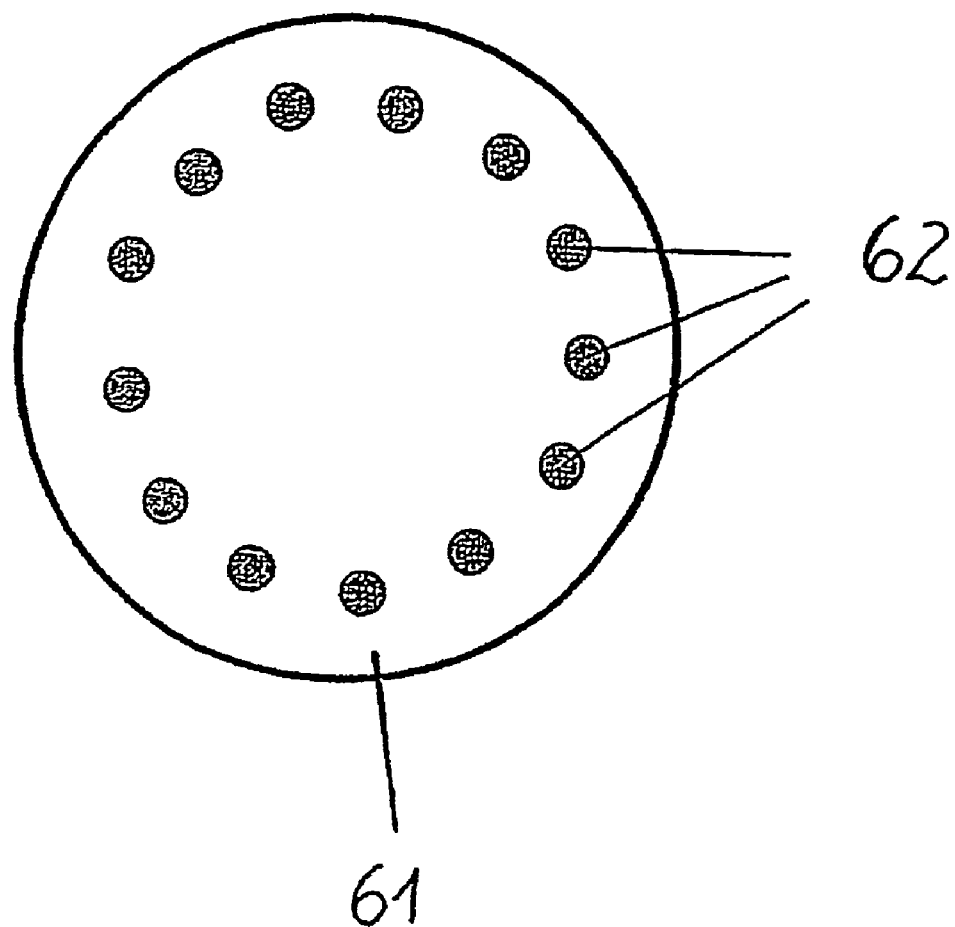

It is also possible for a plurality of (identical or different) reagents to be applied to a support. One example of such an embodiment in the form of a disk is shown in FIG. 4. A plurality of reagent spots (62) is disposed on the optically transparent support (61).

Figure 5:
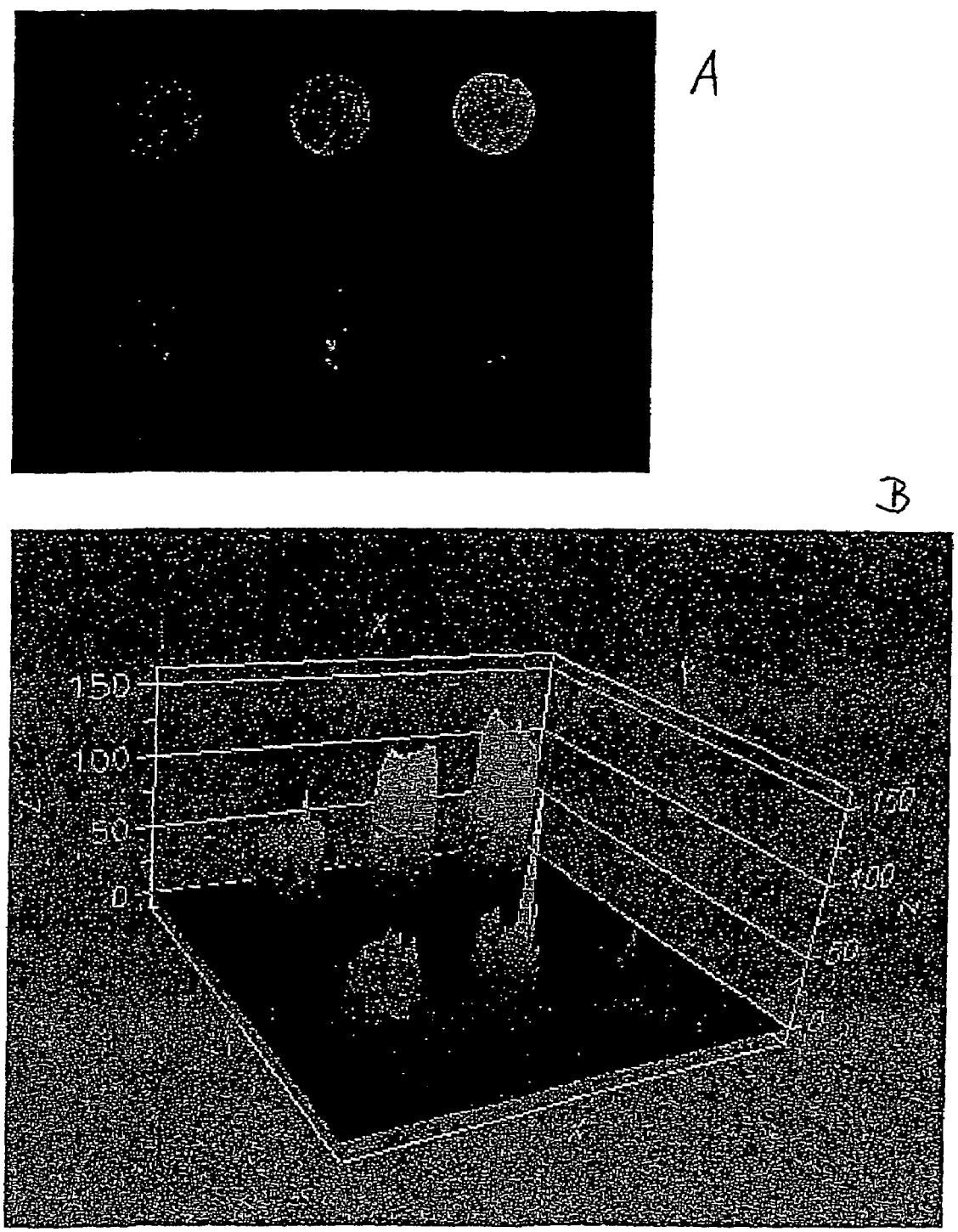

FIGS. 5A and 5B show the fluorescence of a detection system of the invention (glucose dehydrogenase and $NAD^+$) with increasing glucose concentration under a CCD camera.

EXAMPLES

Example 1

Stoichiometric Detection of Glucose in the Glucose Dehydrogenase (GlucDH)/$NAD^+$ System in a Cuvette 100 mg/ml GlucDH are dissolved in buffer of pH 7 and mixed with the appropriate amount of $NAD^+$. On addition of increasing amounts of glucose, an increase in the fluorescence can be detected visually under a UV lamp (excitation wavelength 366 nm) (FIGS. 5A and 5B).

The solution with the enzyme system does not fluoresce without glucose. Nor do glucose and $NAD^+$ result in any fluorescence.

Example 2

Detection of Glucose in the GlucDH/$NAD^+$ System in a Polymer Film

A suspension of the following substance was mixed in a plastic test tube

| Formula 1 | | |
|---|---|---|
| Substance | Amount [g] | Weight [%] |
| Acrylamide | 2.5 | 22.02 |
| Methylenebisacrylamide | 0.7 | 6.17 |
| 2,2-Dimethoxy-2-phenylacetophenone | 0.05 | 0.44 |
| Glycerol | 5 | 44.05 |
| Hydroxyethyl methacrylate | 1.4 | 12.33 |
| Methyl methacrylate | 0.4 | 3.52 |
| Crodasinic O solution, pH 8, 0.3 g/1000 ml | 1 | 8.81 |
| N,N'-(1,2-Dihydroxyethylene)bisacrylamide | 0.3 | 2.64 |
| TOTAL | 11.35 | 100 |

0.5 ml of this suspension were mixed with 0.5 ml of a solution of GlucDH (100 mg/ml), and the mixture was homogenized free of air bubbles in an ultrasonic bath.

The clear solution was poured onto a corona-treated polycarbonate sheet 125 mm thick and illuminated with a conventional illumination apparatus (Isel UV illumination device 2) for 20 min. The sheet was briefly washed with water and then dried in the air.

The resulting layer thickness was <2 μm A freshly prepared glucose/$NAD^+$ solution (GKL-3 solution, 300 mg/dl glucose, 1 ml/6.4 mg of $NAD^+$) was spotted on the film. A strong fluorescence was immediately visible under a UV lamp.

Example 3

Adding a UV Absorber to Influence the Layer Thickness

A polymer layer comprising a blue dye (absorption maximum ≈650 nm) for better identification was produced (formula 2). In a further experiment, a yellow dye was admixed as UV absorber to the initial formula (formula 3).

| Formula 2 | | |
|---|---|---|
| Substance | Amount | Weight [%] |
| Acrylamide | 37.5 g (0.53 mol) | 25.78 |
| Polyethylene glycol diacrylate, Mw ≈ 575 g/mol | 52.5 g (ca. 0.96 mol) | 36.10 |
| Solution of Crodasinic O (0.3 g/1 l) | 50 g | 34.38 |
| 4-Vinylbenzenesulfonic acid | 5 g | 3.44 |
| 2,2-Dimethoxy-2-phenylacetophenone photoinitiator | 350 mg | 0.24 |
| New methylene blue N | 100 mg | 0.06 |
| TOTAL | 145.45 g | 100 |

The mixture was homogenized by stirring and by ultrasonic bath treatment, distributed with a pipette on a 140 μm Pokalon sheet (corona-treated, stage 4) and illuminated in a UV illumination device (Actina U4, W. Lemmen GmbH) for 1 min.

The resulting layer thickness was measured with a screw gage and was 240.5 μm.

| Formula 3 | | |
|---|---|---|
| Substance | Amount | Weight [%] |
| Formula 2 | 1 ml | Ca. 99.99 |
| Mordant Yellow 7 (No. 686) (UV absorber) | 0.0001 g | 0.001 |
| TOTAL | Ca. 1.0001 g | 100 |

The mixture was distributed on a sheet and then polymerized as described above. The resulting layer thickness was measured with a screw gage and was 79.3 μm.

This experiment shows that it is possible to influence the layer thickness. With reaction conditions which were otherwise the same, the layer thickness without UV absorber is 240.5 μm (see above); only 79.3 μm with UV absorber (Mordant Yellow 7).

The invention claimed is:

1. A method for detecting an analyte in a sample by an enzymatic reaction, comprising the steps:
   (a) contacting the sample with a detection reagent comprising an enzyme-coenzyme complex, under conditions with which no regeneration of coenzyme takes place, whereby the enzyme-coenzyme complex is employed in an at least stoichiometric amount relative to the analyte present in the sample, and
   (b) detecting a reaction of the analyte through a change in the enzyme-coenzyme complex.

2. The method as claimed in claim 1, characterized in that the enzymatic reaction comprises a redox reaction.

3. The method as claimed in claim 1, characterized in that an oxidoreductase is used as enzyme, and a change in the coenzyme due to oxidation or reduction is detected.

4. The method as claimed in claim 3, characterized in that the enzyme used is a dehydrogenase selected from a glucose dehydrogenase (E.C.1.1.1.47).

5. The method as claimed in claim 1, characterized in that a coenzyme selected from nicotine derivatives is used.

6. The method as claimed in claim 5, characterized in that the coenzyme is $NAD^+$.

7. The method as claimed in claim 1, 2, 3, 4, 5 or 6, characterized in that the change in the coenzyme is detected by optical methods.

8. The method as claimed in claim 7, characterized in that the change in the coenzyme is detected by measuring absorption, fluorescence, circular dichroism, optical rotary dispersion or refractometry.

9. The method as claimed in claim 8, characterized in that the change in the coenzyme is detected by measuring the fluorescence.

10. The method as claimed in claim 1, characterized in that a gel matrix with an enzyme-coenzyme complex embedded therein is used as detection reagent.

11. The method as claimed in claim 10, characterized in that the gel matrix has a layer thickness of $\leq 50$ μm.

12. The method as claimed in claim 10 or 11, characterized in that a gel matrix based on photo-polymerizable substances is used.

13. The method as claimed in claim 1, characterized in that an analyte in a body fluid is determined.

14. The method as claimed in claim 13, characterized in that a determination of glucose in blood is carried out.

15. The method as claimed in claim 1, characterized in that the duration of the reaction of the analyte is $\leq 5$ s.

16. The method as claimed in claim 1, characterized in that the reaction is carried out in the absence of mediators able to react with the coenzyme.

17. A method for detecting an analyte in a sample by an enzymatic reaction, comprising the steps:
   contacting the sample with a detection reagent comprising a detection reagent comprising an enzyme-coenzyme complex in a form such that no regeneration of the coenzyme takes place, whereby the enzyme-coenzyme complex is employed in an at least stoichiometric amount relative to the analyte present in the sample, and a support to receive the detection reagent, under conditions with which no regeneration of coenzyme takes place, and
   detecting a reaction of the analyte through a change in the enzyme-coenzyme complex.

* * * * *